United States Patent
Carati et al.

(10) Patent No.: US 9,358,531 B2
(45) Date of Patent: Jun. 7, 2016

(54) PROCESS FOR THE PREPARATION OF TS-1 ZEOLITES

(75) Inventors: Angela Carati, San Giuliano Milanese (IT); Donatella Berti, San Donato Milanese (IT); Roberto Millini, Cerro Al Lambro (IT); Franco Rivetti, Milan (IT); Maria Angela Mantegazza, Cambiago (IT); Gianni Girotti, Novara (IT)

(73) Assignee: POLIMERI EUROPA S.p.A., San Donato Milanese (IT)

(*) Notice: Subject to any disclaimer, the term of this patent is extended or adjusted under 35 U.S.C. 154(b) by 1166 days.

(21) Appl. No.: 12/808,080

(22) PCT Filed: Dec. 3, 2008

(86) PCT No.: PCT/EP2008/010290
§ 371 (c)(1),
(2), (4) Date: Sep. 16, 2010

(87) PCT Pub. No.: WO2009/077086
PCT Pub. Date: Jun. 25, 2009

(65) Prior Publication Data
US 2010/0331576 A1    Dec. 30, 2010

(30) Foreign Application Priority Data

Dec. 14, 2007  (IT) .............................. MI2007A2342

(51) Int. Cl.
| | | |
|---|---|---|
| C01B 39/08 | (2006.01) |
| C01B 37/00 | (2006.01) |
| B01J 29/89 | (2006.01) |
| B01J 35/02 | (2006.01) |
| C07C 249/04 | (2006.01) |

(52) U.S. Cl.
CPC ................ *B01J 29/89* (2013.01); *B01J 35/023* (2013.01); *C01B 37/005* (2013.01); *C01B 39/085* (2013.01); *C07C 249/04* (2013.01)

(58) Field of Classification Search
CPC ....... C01B 39/085; C01B 37/005; B01J 29/89
See application file for complete search history.

(56) References Cited

U.S. PATENT DOCUMENTS

| | | | |
|---|---|---|---|
| 4,410,501 A * | 10/1983 | Taramasso et al. ........... 423/705 |
| 5,958,369 A | 9/1999 | Kosuge et al. |
| 2001/0002991 A1* | 6/2001 | Botti et al. .................... 423/707 |
| 2003/0152510 A1* | 8/2003 | Senderov et al. ............. 423/713 |
| 2007/0059237 A1* | 3/2007 | Miller ........................... 423/700 |
| 2008/0138619 A1 | 6/2008 | Miller |
| 2008/0146827 A1 | 6/2008 | Miller |
| 2008/0292542 A1 | 11/2008 | Miller |

FOREIGN PATENT DOCUMENTS

| | | |
|---|---|---|
| EP | 1 106 576 | 6/2001 |
| FR | 2 471 950 | 6/1981 |
| JP | 08253314 | 10/1996 |
| JP | 2000 185912 | 7/2000 |
| JP | 2007 145687 | 6/2007 |
| JP | 2007145687 | * 6/2007 |

OTHER PUBLICATIONS

Zhang, Guangyu et al., "Preparation of Colloidal Suspensions of Discrete TS-1Crystals", Chem. Mater., vol. 9, No. 1, pp. 210-217, (1997).

* cited by examiner

*Primary Examiner* — David M Brunsman
(74) *Attorney, Agent, or Firm* — Oblon, McClelland, Maier & Neustadt, L.L.P.

(57) ABSTRACT

The invention relates to a new process which allows the preparation of TS-1 zeolites in a pure phase and with a crystallinity higher than 95%, operating at reduced reaction volumes, and obtaining high productivities and extremely high crystallization yields. The particular crystalline form of the TS-1 zeolite thus prepared, is also described.

13 Claims, 2 Drawing Sheets

TS1 107/159
200KV
50.00 nm

PROCESS FOR THE PREPARATION OF TS-1 ZEOLITES

CROSS REFERENCE TO RELATED APPLICATION

This application is a 371 of PCT/EP2009/010290, filed on Dec. 3, 2008, and claims priority to Italian Patent Application No. MI 2007 A 002342, filed on Dec. 14, 2007.

The present invention relates to a new process which, with high crystallization yields, high productivities and using reduced reaction volumes, allows TS-1 zeolites to be prepared in pure phase and with a crystallinity higher than 95%. The present invention also relates to the particular crystalline form of the TS-1 zeolites thus prepared.

In general, the hydrothermal synthesis of zeolites includes the following preparation steps:
 a) preparation of the reagent mixture
 b) hydrothermal crystallization treatment
 c) separation of the crystalline phase from the crystallization mother liquor.
 d) drying.

The end-product obtained is then subjected to subsequent thermal treatment and possible post-treatment selected according to the final application. In the case of the TS-1 zeolite described for the first time in U.S. Pat. No. 4,410,501, a reaction mixture is used in step a) having the following composition expressed as molar ratios:
 Si/Ti=5-200
 TPA-OH/Si=0.1-2
 H$_2$O/Si=20-200

The TS-1 zeolite is characterized, in its calcined and anhydrous form, by the following formula:

$$x\text{TiO}_2.(1-x)\text{SiO}_2$$

wherein x ranges from 0.0005 to 0.04, preferably from 0.01 to 0.025.

This zeolite shows excellent catalytic characteristics in oxidation reactions, such as, for example, the epoxidation of olefins, hydroxylation of aromatic compounds, oximation of ketones and oxidation of alcohols.

In U.S. Pat. No. 4,410,501, the H$_2$O/Ti ratio which can be calculated from the examples, which represents the dilution condition at which this preparation process of TS-1 zeolite is effected, is about 1050 (example 1) and about 505 (example 2). The synthesis is carried out at a temperature ranging from 130 to 200° C. over a period of 6 to 30 days.

In patent application EP 906,784, a new synthesis is subsequently described, under more concentrated conditions, with reference to the H$_2$O/Si ratio. In particular, the composition of the reaction mixture used in this case, is the following:
 Si/Ti=35-2,000
 TPA-OH/Si=0.2-0.5
 H$_2$O/Si=10-35

The H$_2$O/Ti ratio which can be calculated from example 1 proves to be 679.

The synthesis is carried out at a temperature ranging from 190 to 230° C. for a time of 0.5 to 10 hours. This synthesis, with respect to the results previously obtained, allows a yield of the zeolite crystallization of up to 100% to be obtained, for example ranging from 98 to 100%. The crystallization yield corresponds to the percentage of solid product obtained, considering as 100%, the weight which would be obtained if all the titanium and silicon present in the reagent mixture precipitated in the form of oxides. A crystallization yield of 100% therefore corresponds to a total recovery in the zeolite of the all silica and titanium present in the reagent mixture.

Subsequently, in patent application EP 1,106,576, among other things, a synthesis of zeolites is described, selected from the group consisting of MFI, MEL and MFI/MEL zeolites. The zeolites are preferably selected from the following group:
 MFI zeolites having the formula $$p\text{HMO}_2.q\text{TiO}_2.\text{SiO}_2$$

wherein M is a metal selected from aluminium, gallium and iron, p has a value ranging from 0 to 0.04 and q has a value ranging from 0.0005 to 0.03,
 MFI zeolites having the formula $$a\text{Al}_2\text{O}_3.(1-a)\text{SiO}_2$$

wherein a has a value of 0 to 0.02,
 MEL or MFI/MEL zeolites having the formula $$x\text{TiO}_2.(1-x)\text{SiO}_2$$

wherein x has a value of 0.0005 to 0.03.

The preparation can be effected even under more concentrated conditions with respect to those described in the prior document with reference to the H$_2$O/Si ratio. In particular, the composition of the reaction mixture used is the following:
 Ti/Si=0-0.03
 M/Si=0-0.04 wherein M can be selected form Al, Fe and Ga
 TPA-OH/Si=0.2-0.5
 H$_2$O/Si=4-35

The synthesis is carried out at a temperature ranging from 150 to 230° for a time of 0.5 to 48 hours, in the absence of alkaline metals.

A new process has now been found, which, by operating at a particularly low dilution, with suitable molar ratios between water and titanium in the reaction mixture, allows TS-1 zeolites to be prepared, in pure phase, with a crystallinity higher than 95%, contemporaneously obtaining a high productivity and high crystallization yield. The TS-1 zeolite thus prepared has a particular crystalline form.

An object of the present invention therefore relates to a process for preparing TS-1 zeolites, which comprises subjecting a mixture containing a silicon source, a titanium source and tetrapropyl ammonium hydroxide, having the following composition as molar ratios:
 Si/Ti=35-150
 TPA-OH/Si=0.2-0.5 wherein TPA=tetrapropylammonium
 H$_2$O/Si=higher than or equal to 4 and lower than 10
 H$_2$O/Ti=higher than or equal to 320
to hydrothermal treatment at autogenous pressure, at a temperature ranging from 190 to 230° C. and for a time of 0.5 to 10 hours, in the absence of alkaline metals.

A particularly preferred aspect is to operate at a H$_2$O/Ti molar ratio higher than or equal to 320 and lower than or equal to 600.

The silicon source can be selected from silica gel, colloidal silicas or tetraalkyl orthosilicates, preferably tetra-ethyl orthosilicates.

The titanium source can be selected from hydrolyzable titanium compounds, such as halides and tetraalkyl orthotitanates, preferably tetra-ethyl orthotitanate.

The reagent mixture can crystallize both under static conditions and under stirring.

At the end of crystallization, crystals are isolated, for example by means of centrifugation, then the crystals are subjected to drying at a temperature of between 100 and 150° C., during a time of 1 to 15 hours. After drying, the material can be calcined at temperatures of between 500 and 600° C. during a time of 2 to 10 hours.

The material obtained after calcination is analyzed by X-ray powder diffraction, registered by means of a vertical goniometer equipped with an electronic impulse counting system, using CuKα radiation (λ=1.54178 Å). Upon XRD analysis, the crystalline phase proves to consist of a phase with a structure of the pure MFI type and has a crystallinity of over 95%, preferably over 98%, even more preferably 100%.

The crystallinity is evaluated from the ratio between the integrated intensities of some intense reflections present in the XRD spectrum of the TS-1 sample ($I_x$) under examination and the corresponding reflections present in the XRD spectrum of a standard TS-1 sample ($I_{std}$), according to the relationship:

$$\text{crystallinity \%} = (I_x/I_{std}) \times 100$$

The reflections typically used are those within the angular range of 22-25.5° 2 theta.

It is also possible to calculate from the XRD spectrum, on the basis of the parameters and volume of the elementary cell, the molar ratio between silica and titanium of the zeolite framework, as described by M. Taramasso, G. Perego and B. Notari in U.S. Pat. No. 4,410,501 (1983).

The TS-1 thus obtained is characterized by a $SiO_2/TiO_2$ molar ratio of the zeolite framework generally within the range of about 40 to about 200.

The new synthesis allows the preparation of TS-1 with a very high crystallization yield, higher than 90%, preferably higher than 95%. The productivity which can be obtained with the process of the present invention, intended as the percentage of solid product obtained with respect to the weight of the reagent mixture used ranges from about 12% to about 18%.

The TS-1 zeolite prepared by means of this synthesis is characterized by crystals having an elongated hexagonal form in which the major axis ranges between 400 and 50 nm.

The TS-1 in this particular crystalline form is new and is a further object of the present invention.

After the separation of the crystalline phase, in any of the subsequent preparation steps, the crystalline phase can be mixed with a binding phase or with a precursor of the binding phase and then subjected to a forming treatment, selected by the expert in relation to the desired application.

According to a preferred aspect of the present invention, microspheres containing oligomeric silica and TS-1 zeolite, prepared according to the process of the present invention, are obtained by subjecting the suspension containing the zeolite crystals directly resulting from the hydrothermal synthesis, to rapid drying, as described in EP 906 784 and in EP 1 106 576. In particular, in accordance with EP 906 784, tetraalkyl orthosilicate is added to the suspension containing the zeolite crystals obtained by means of the process of the present invention, before subjecting it to rapid drying. The tetraalkyl orthosilicate is preferably added in a quantity of 0.08 to 0.50 moles per 100 grams of zeolite contained in said suspension. The resulting microspheres are subjected to calcination.

According to EP 1 106 576, an oligomeric silica sol, obtained by the hydrolysis of a tetraalkyl orthosilicate in the presence of tetraalkyl ammonium hydroxide, is added to the suspension of TS-1 zeolite crystals obtained by means of the process of the present invention, before feeding it to the rapid drying. The oligomeric silica is preferably prepared through hydrolysis, at a temperature ranging from 20 to 120° C. and for a time of 0.2 to 24 hours, of a mixture comprising a silica source, possibly an aluminium source, a tetraalkyl ammonium hydroxide (TAA-OH), having the following molar composition:

TAA-OH/$SiO_2$=0.04-0.40
$H_2O$/$SiO_2$=10-40
$Al_2O_3$/$SiO_2$=0-0.02

The oligomeric silica sol and the suspension deriving from the synthesis of the zeolite, are preferably mixed in an oligomeric silica/zeolite weight ratio ranging from 0.05 to 0.70. The resulting mixture is treated under stirring, at a temperature ranging from 25° C. to the boiling point of the mixture itself, for a time of 1 to 48 hours, and it is then subjected to rapid drying by means of a spray-drier and the resulting microspheres are calcined.

The microspheres prepared using the method described above preferably have a diameter ranging from 5 to 300 μm. They contain oligomeric silica and the zeolite crystals having an elongated hexagonal form described above, preferably in a weight ratio varying from 0.05 to 0.70, preferably between 0.05 and 0.30.

The zeolite prepared according to the process of the present invention and the catalysts containing it, preferably in the form of microspheres, can be used, for example, for the conversion of olefins to epoxides, for the hydroxylation of aromatic products and for the oximation of ketones.

EXAMPLE 1

Two solutions are prepared, having the following composition:

Solution A: 50 g of demineralized $H_2O$ mixed with 200.3 g of TPAOH at 40% w/w (Sachem)

Solution B: 3.96 g of Tetra-ethyl-orthotitanate (Fluka) mixed with 360.4 g of Tetra-ethyl-orthosilicate (Dynasil Nobel).

The molar ratios in the reagent mixture are indicated hereunder:

Si/Ti=99.6
TPAOH/Si=0.23
$H_2O$/Si=5.5
$H_2O$/Ti=547.8

Solution A is charged into a 1-liter autoclave equipped with an anchor stirrer, the stirring rate being regulated at a peripheral rate of 10 m/min. Solution B is then charged and the autoclave is heated to 200° C. for 2 hours. At the end of the crystallization, a milky suspension is discharged, which is centrifuged, the solid fraction is washed with demineralized water, dried at 150° C. for 1 hour and calcined at 550° C. in air for 5 hours.

102 g of solid product are obtained, corresponding to a crystallization yield of 97% and with a process productivity equal to 17%.

XRD analysis was effected with a Philips X'PERT diffractometer equipped with a proportional impulse counter and a secondary monochromator, with graphite curved crystal. The data were collected within the spectrum range of 20≤2θ≤50°, with steps of 0.02° 2θ and accumulation times of 30 s/step; the radiation was CuKα (λ=1.54178 Å). The sample proves to consist of a pure MFI phase with a crystallinity of 100%.

For the UV-Vis analysis, a Perkin-Elmer Lambda 9 spectrophotometer was used, equipped with a reflectance sphere.

The sample has a signal with a maximum at 200 nm, typical of isolated titanium in a tetrahedral coordination.

The sample has a $SiO_2/TiO_2$ molar ratio=109, determined on the basis of the expansions of the reticular parameters evaluated by means of XRD.

Figure 1:
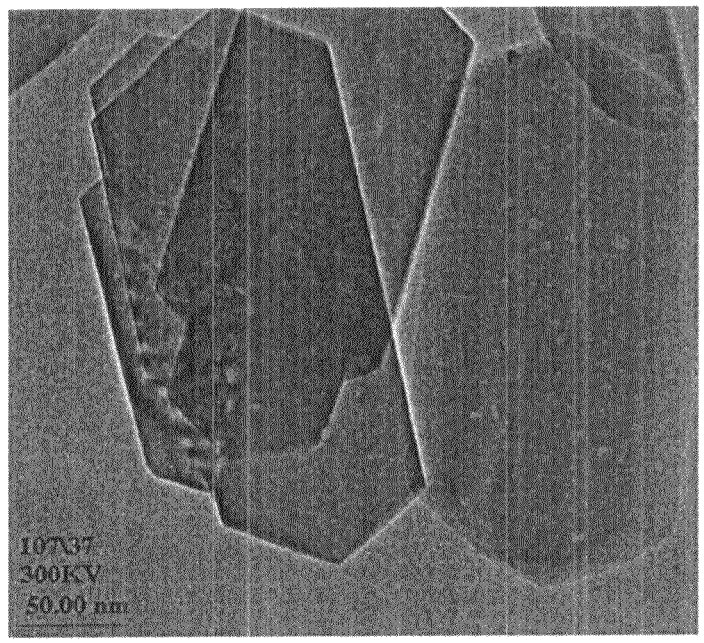
FIG. 1 is a TEM image of crystals produced in Example 1.

The TEM image obtained with a Philips EM420 transmission electron microscope, operating with an electron acceleration potential of 120 kV, is shown in FIG. 1. The presence of crystals can be observed, having an elongated hexagonal form in which the major axis is about 300 nm.

EXAMPLE 2

Two solutions are prepared having the following composition:

Solution A: 93.4 g of demineralized $H_2O$ mixed with 200.3 g of TPAOH at 40% w/w (Sachem).

Solution B: 7.9 g of Tetra-ethyl-orthotitanate (Fluka) mixed with 360.3 g of tetra-ethyl-orthosilicate (Dynasil Nobel)

The molar ratios in the reagent mixture are indicated hereunder:

Si/Ti=49.9
TPAOH/Si=0.23
$H_2O$/Si=6.9
$H_2O$/Ti=344.3

Solution A is charged into a 1-liter autoclave equipped with an anchor stirrer, the stirring rate is regulated at a peripheral rate of 10 m/min. Solution B is then charged and the autoclave is heated to 200° C. for 2 hours. At the end of the crystallization, a milky suspension is discharged, which is centrifuged; the solid fraction is washed with demineralized water, dried at 150° C. for 1 hour and calcined at 550° C. in air for 5 hours.

101 g of solid product are obtained, corresponding to a crystallization yield of 96% and a process productivity equal to 15%.

Upon XRD analysis, the sample proves to consist of a phase with a structure of the pure MFI type, with a 100% crystallinity.

Upon UV-Vis analysis, the sample has a signal with a maximum at 200 nm, typical of isolated titanium in a tetrahedral coordination.

The sample has a $SiO_2/TiO_2$ molar ratio=54, determined on the basis of the expansion of the reticular parameters evaluated by means of XRD.

Figure 2:
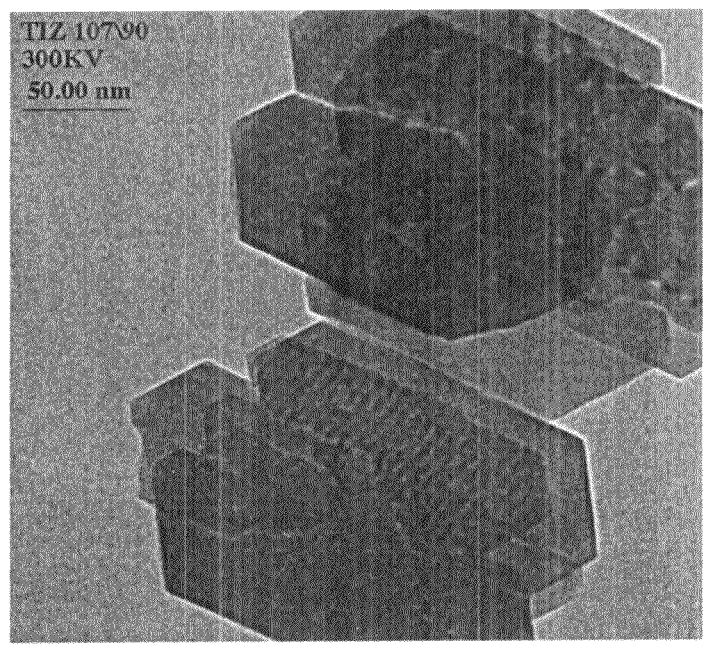
FIG. 2 is a TEM image of crystals produced in Example 2.

The TEM image is shown in FIG. 2. The presence can be observed of crystals having an elongated hexagonal form, in which the major axis is in the order of 200 nm.

EXAMPLE 3 (COMPARATIVE)

Two solutions are prepared, having the following composition:

Solution A: 128.7 g of demineralized $H_2O$ mixed with 200.3 g of TPAOH at 40% w/w (Sachem).

Solution B: 9.9 g of Tetra-ethyl-orthotitanate (Fluka) mixed with 360.3 g of tetra-ethyl-orthosilicate (Dynasil Nobel).

The molar ratios in the reagent mixture are indicated hereunder:

Si/Ti=39.8
TPAOH/Si=0.23
$H_2O$/Si=8.0
$H_2O$/Ti=318.4

Solution A is charged into a 1-liter autoclave equipped with an anchor stirrer, the stirring rate is regulated at a peripheral rate of 10 m/min. Solution B is then charged and the autoclave is heated to 200° C. for 2 hours. At the end of the crystallization, a gel is discharged, which is centrifuged; the solid fraction is washed with demineralized water, dried at 150° C. for 1 hour and calcined at 550° C. in air for 5 hours.

Upon XRD analysis, the sample has a crystallinity of 91%.

EXAMPLE 4

Two solutions are prepared, having the following composition:

Solution A: 134.9 g of demineralized $H_2O$ mixed with 200.4 g of TPAOH at 40% w/w (Sachem).

Solution B: 10.0 g of Tetra-ethyl-orthotitanate (Fluka) mixed with 360.4 g of tetra-ethyl-orthosilicate (Dynasil Nobel).

The molar ratios in the reagent mixture are indicated hereunder:

Si/Ti=39.5
TPAOH/Si=0.23
$H_2O$/Si=8.2
$H_2O$/Ti=323.9

Solution A is charged into a 1-liter autoclave equipped with an anchor stirrer, the stirring rate is regulated at a peripheral rate of 10 m/min. Solution B is then charged and the autoclave is heated to 200° C. for 2 hours. At the end of the crystallization, a milky suspension is discharged, which is centrifuged; the solid fraction is washed with demineralized water, dried at 150° C. for 1 hour and calcined at 550° C. in air for 5 hours.

103 grams of solid product are obtained, corresponding to a crystallization yield of 97% and at a process productivity of 15%.

Upon XRD analysis, the sample proves to consist of a phase with a structure of the pure MFI type, with a 100% crystallinity.

Upon UV-Vis analysis, the sample has a signal with a maximum at 200 nm, typical of isolated titanium in a tetrahedral coordination.

The sample has a $SiO_2/TiO_2$ molar ratio=45, determined on the basis of the expansion of the reticular parameters evaluated by means of XRD.

Figure 3:
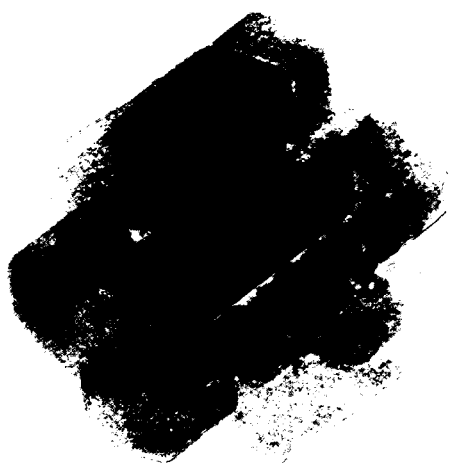
FIG. 3 is a TEM image of crystals produced in Example 4.

The TEM image is shown in FIG. 3. The presence can be observed of crystals having an elongated hexagonal form, in which the major axis is in the order of 120 nm.

EXAMPLE 5

The TS-1 zeolite prepared in example 4 was tested in an ammoximation reaction of cyclohexanone to cyclohexanone-oxime.

0.43 g of the catalyst synthesized as described in example 4, 25 ml of aqueous ammonia (at 15% by weight), 25 ml of t-butanol and 9.74 g of cyclohexanone, are charged, in an inert atmosphere, into a jacketed glass reactor equipped with a mechanical stirrer.

The suspension is heated to 78° C. and 11.84 g of an aqueous solution of $H_2O_2$ at 30.81% by weight are added, under stirring, over a period of 50 minutes. At the end of the reaction, the suspension is filtered and the solution is analyzed by gas-chromatography.

A conversion of cyclohexanone of 52.5% moles is observed and a selectivity to oxime of 36.3%. The $H_2O_2$ yield is 17.6%.

At the end of the reaction, a conversion of cyclohexanone of 58.9% is observed, a molar selectivity to oxime of 64.3%, based on the converted cyclohexanone, and a molar yield to oxime, based on the cyclohexanone reacted, of 37.9%.

The invention claimed is:

1. A process for preparing TS-1 zeolite crystals, the process comprising hydrothermally treating a mixture consisting essentially of:
   a silicon source;
   a titanium source; and
   tetrapropyl ammonium hydroxide (TPA-OH)
at autogenous pressure, at a temperature ranging from 190 to 230° C., and for a time of 0.5 to 10 hours, in the absence of alkaline metals, thereby obtaining TS-1 zeolite crystals having a crystallinity higher than 95% and a crystallization yield higher than 90%, wherein
   the mixture has the following composition as molar ratios:
   Si/Ti=35-150;
   TPA-OH/Si=0.2-0.5;
   $H_2O$/Si=from 4 to less than 10; and
   $H_2O$/Ti=from 320 to 600.

2. The process according to claim 1, further comprising, after the hydrothermally treating, isolating, drying, and then calcinating the TS-1 zeolite crystals.

3. The process according to claim 2, wherein the drying is carried out at a temperature ranging from 100 to 150° C., for a time ranging from 1 hour to 15 hours, and the calcinating is carried out at a temperature ranging from 500 to 600° C. for a time ranging from 2 to 10 hours.

4. The process according to claim 1, wherein the silica source is at least one selected from the group consisting of silica gel, colloidal silicas, and tetraalkyl orthosilicates.

5. The process according to claim 4, wherein the silicon source is tetraethyl orthosilicate.

6. The process according to claim 1, wherein the titanium source is at least one selected from the group consisting of titanium halides and tetraalkyl orthotitanates.

7. The process according to claim 6, wherein the titanium source is tetraalkyl orthotitanate.

8. The process according to claim 1, further comprising isolating the zeolite crystals, mixing the zeolite crystals with a binding phase or a binding phase precursor, and forming a binded zeolite form.

9. The process according to claim 1, further comprising rapidly drying a mixture resulting after the hydrothermally treating, comprising tetraalkyl orthosilicate, by a spray-drier to obtain microspheres, and calcinating the resulting microspheres.

10. The process according to claim 1, further comprising:
   adding an oligomeric silica sol obtained from a hydrolysis of a tetraalkyl orthosilicate in the presence of tetraalkyl ammonium hydroxide to a mixture resulting after the hydrothermally treating, which is kept under stirring at a temperature ranging from 25° C. to its boiling point, for a period of 1 to 48 hours to obtain a second mixture;
   then rapidly drying the second mixture by a spray-drier to obtain microspheres; and
   the calcinating resulting microspheres.

11. The process according to claim 10, wherein the oligomeric silica sol is prepared by the hydrolysis, at a temperature ranging from 20 to 120° C. and for a time ranging from 0.2 to 24 hours, of a mixture comprising:
   a silica source;
   optionally, an aluminum source; and
   a tetraalkyl ammonium hydroxide (TAA-OH),
having a following molar composition:
   TAA-OH/$SiO_2$=0.04-0.40;
   $H_2O$/$SiO_2$=10-40; and
   $Al_2O_3$/$SiO_2$=0-0.02.

12. The process according to claim 1, wherein the TS-1 zeolite crystals have a crystallinity of higher than 98%.

13. A process for preparing TS-1 zeolite crystals, the process comprising hydrothermally treating a mixture comprising:
   a silicon source;
   a titanium source; and
   tetrapropyl ammonium hydroxide (TPA-OH)
   at autogenous pressure, at a temperature ranging from 190 to 230° C., and for a time of 0.5 to 10 hours, in the absence of alkaline metals, thereby obtaining TS-1 zeolite crystals having a crystallinity higher than 95% and a crystallization yield higher than 90%, wherein
   the mixture has the following composition as molar ratios:
   Si/Ti=35-150;
   TPA-OH/Si=0.2-0.5;
   $H_2O$/Si=from 4 to less than 10; and
   $H_2O$/Ti=from 320 to 600.

* * * * *